(12) United States Patent
Spickermann et al.

(10) Patent No.: US 10,603,420 B2
(45) Date of Patent: Mar. 31, 2020

(54) BLOOD TREATMENT DEVICE WITH MEMBRANED HEAT EXCHANGER, AND DEVICE FOR DETECTING A FLUID LEAK

(71) Applicant: FRESENIUS MEDICAL CARE DEUTSCHLAND GMBH, Bad Homburg (DE)

(72) Inventors: Reiner Spickermann, Burghausen (DE); Klaus Balschat, Schwebheim (DE); Tilman Staeblein, Wuerzburg (DE); Arne Peters, Bad Homburg (DE); Peter Kloeffel, Nuedlingen (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 105 days.

(21) Appl. No.: 15/576,129

(22) PCT Filed: May 19, 2016

(86) PCT No.: PCT/EP2016/000835
§ 371 (c)(1),
(2) Date: Nov. 21, 2017

(87) PCT Pub. No.: WO2016/184572
PCT Pub. Date: Nov. 24, 2016

(65) Prior Publication Data
US 2018/0207343 A1 Jul. 26, 2018

(30) Foreign Application Priority Data

May 21, 2015 (DE) .................. 10 2015 006 601

(51) Int. Cl.
*A61M 1/16* (2006.01)
*A61M 31/00* (2006.01)
(Continued)

(52) U.S. Cl.
CPC ....... *A61M 1/1662* (2014.02); *A61M 2205/15* (2013.01); *F28D 2021/005* (2013.01)

(58) Field of Classification Search
USPC .......... 210/23, 87, 90, 137, 149, 195.2, 251, 210/321, 434, 638, 639, 645, 650, 651, (Continued)

(56) References Cited

U.S. PATENT DOCUMENTS

2011/0198289 A1* 8/2011 Jonsson ............. A61M 1/3621
  210/650
2014/0112828 A1* 4/2014 Grant .................. A61M 1/3652
  422/44

FOREIGN PATENT DOCUMENTS

DE 102007041766 3/2009
WO WO 2010/040819 4/2010
WO WO 2012/053958 4/2012

* cited by examiner

*Primary Examiner* — Hayden Brewster
(74) *Attorney, Agent, or Firm* — Jacobson Holman, PLLC.

(57) ABSTRACT

A blood treatment device includes a heat exchanger having a first space and a second space, with a first fluid flowing through the first space and a second fluid flowing through the second space. The heat exchanger has a membrane which separates the first space from the second space, with the membrane forming a component of a capacitor having two capacitor plates, between which the membrane is located. A monitoring means is connected to the capacitor, and is configured to detect an electrical property of the capacitor, for the purpose of detecting a fluid leak from the first space to the second space.

17 Claims, 3 Drawing Sheets

(51) Int. Cl.
  *C02F 9/00* (2006.01)
  *B01D 61/00* (2006.01)
  *F28D 21/00* (2006.01)
(58) Field of Classification Search
  USPC .................................. 210/660, 767, 774, 775
  See application file for complete search history.

BLOOD TREATMENT DEVICE WITH MEMBRANED HEAT EXCHANGER, AND DEVICE FOR DETECTING A FLUID LEAK

BACKGROUND OF THE INVENTION

Field of the Invention

The present invention relates to a blood treatment device having at least one heat exchanger which has at least one space and at least one second space, wherein, in the operation of the blood treatment device, the first space is flowed through by at least one first fluid and the second space is flowed through by at least one second fluid, and wherein the heat exchanger has at least one membrane which separates the named first space from the named second space.

The invention thus relates to a blood treatment device, in particular to a dialysis device, having at least one heat exchanger or recuperator. The heat exchanger has at least two media spaces which are separated from one another by at least one heat-recuperating membrane.

SUMMARY OF THE INVENTION

Against the background of minimizing the probability of a contamination of the first fluid by the second fluid, or vice versa, it is the object of the present invention to further develop a blood treatment device of the initially named kind such that a possible leak through the membrane and thus a hydraulic connection of the two media spaces of the heat exchanger is recognized fast and reliably.

This object is achieved by a blood treatment device having the features described herein.

Provision is accordingly made that the membrane forms a component of at least one capacitor which has at least two capacitor plates between which the at least one membrane is located.

Monitoring means are furthermore provided which are connected to the capacitor and which are configured such that they detect at least one electrical or physical property of the capacitor for the purpose of detecting the leak from the first space to the second space.

It is thus the underlying idea of the present invention to detect, by an electrical monitoring, a possible leak through the membrane and thus a hydraulic connection of the two media spaces, i.e. of the first space and of the second space, which may result in a contamination of the fluids.

This electrical monitoring takes place in that the capacitor is monitored with respect to one or more of its electrical or physical properties such as the impedance, the capacitance, an output signal measured at the capacitor, such as a voltage, etc.

If a difference from a desired value or from a desired progression of the respective parameter is determined by the monitoring means, a conclusion on a leak can be drawn and corresponding countermeasures can be taken.

The probability of the administration of a contaminated fluid, for example of a supply liquid, by biological and chemical substances thus approaches zero due to this electrical monitoring of the capacitor or of the membrane.

The monitoring means preferably work continuously, i.e. monitoring is continuous during the operation of the blood treatment device. However, every other type of monitoring such as a monitoring after the end of specific time intervals or at specific times is also covered by the invention.

It is optionally possible to dispense with other, risk-reducing countermeasures due to the monitoring of the membrane of the heat exchanger since the blood treatment device can respond to a detected leak immediately and without the evaluation of further monitoring devices. Provision is thus preferably made that further means for leak monitoring are not present.

An arrangement is conceivable in which both the capacitor plates and the membrane are located between the first space and the second space. In this case, the capacitor plates and the membrane are thus located between the two fluids and a leak in one or both of the capacitor plates and/or of the membrane can be detected.

It is pointed out at this point that the term "capacitor plates" covers any desired element which can be used as a capacitor component independently of whether the element is of plate shape or has a different form.

The case is also covered by the invention that the membrane is located between the first space and the second space and that the first space and the second space are arranged between the capacitor plates.

A capacitor is thus formed overall in whose inner space, i.e. between whose plates, not only the membrane is arranged, but also the first fluid and the second fluid. A dielectric is thus formed whose properties vary in the event of a leak due to the liquid transfer between the primary side and the secondary side, i.e. from the first space into the second space, or vice versa.

The monitoring means can comprise a DC voltage source or an AC voltage source whose poles are connected to the capacitor plates. To detect an electrical property of the capacitor which varies on a leak, the voltage over the capacitor can be detected and a conclusion can be drawn from a variation of e.g. the amplitude, the frequency or a phase shift of the measured voltage with respect to the input voltage or with respect to the voltage in the desired state (i.e. without a leak) that a leak has occurred.

However, the use of a DC voltage source is generally also conceivable. It would e.g. be possible in this case to measure the ohmic resistance of the capacitor and to draw a conclusion on a leak on a change in the resistance.

The two capacitor plates can contact the membrane directly and at both sides so that a sandwich-like structure results.

The capacitor plates preferably comprise metal and in particular stainless steel or titanium.

The membrane is preferably designed as an electrical insulator, but with heat conductivity, so that a good heat transfer is possible between the two spaces of the heat exchanger.

It is conceivable to design the membrane from Kapton. This material is a polyamide. Other polymers or other materials can generally also be used for the membrane.

Any desired electrical or physical properties of the capacitor which vary in the event of a leak can generally be considered as parameters monitored by the monitoring means. The impedance or the capacitance of the capacitor are conceivable as monitored parameters, for example.

It is also conceivable that the capacitor is integrated into a resonant circuit and that the monitoring means are configured such that they carry out a measurement of the resonant frequency of the capacitor.

If the impedance, the capacitance or also the resonant frequency of the capacitor changes, a conclusion can be drawn on a leak of the membrane and/or of the capacitor plate(s).

It is conceivable that the monitoring means comprise at least one measurement resistor over which the voltage is determined.

This measurement resistor can be connected in series with the resistor formed by the membrane.

In a further embodiment of the invention, the monitoring means have a low pass filter for determining an average value of the voltage measured over the capacitor.

Provision can furthermore be made that, for the purpose of checking the monitoring means, at least one test resistor is provided or can be used which is or can be connected in parallel with the resistor formed by the membrane.

This test resistor thus simulates the occurrence of a leak. A check can accordingly be made whether the monitoring means determine a corresponding signal variation with a deployed test resistor. If this is the case, a conclusion can be drawn on the correct operation of the monitoring means.

The blood treatment device is preferably a dialysis device such as a hemodialysis device.

The blood treatment device can be connected to a water supply, wherein the heat exchanger can be connected to the heat supply such that the named first space of the heat exchanger is flowed through by fresh water, in particular by RO water from the water supply.

This fresh water or RO water can be used to prepare a dialysis solution by addition of concentrates.

The second space of the heat exchanger can be arranged such that it is flowed through by consumed, heated dialysis solution. A heat transfer from the consumed dialysis solution to the fresh water thus occurs.

The efficiency of heat exchangers increases inter alia with an increasing temperature resistance between the primary side and the secondary side, i.e. between the two spaces of the heat exchanger. In dialysis devices, the point having the coldest medium temperature is located directly after the water connection or after the water inflow path. As stated, the secondary side, i.e. the other space, can be flowed through by heated dialyzate before it leaves the device in the direction of the outflow.

It is possible by the present invention, in particular with a continuous monitoring or also with a monitoring carried out at time intervals of the heat-exchanging membrane, to respond directly to a leak, for example in that pumps are stopped or valves closed. Since such a direct response is easily possible, it is optionally possible to dispense with other risk-reducing and cost-incurring countermeasures.

The monitoring means can be connected to a display at which the state is displayed which is detected by the monitoring means. Other output means such as acoustic and/or optical means for the information of the user on the occurrence of a leak are also conceivable and covered by the invention, for example.

BRIEF DESCRIPTION OF THE DRAWINGS

Further details and advantages of the invention will be explained in more detail with reference to an embodiment shown in the drawing.

There are shown.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
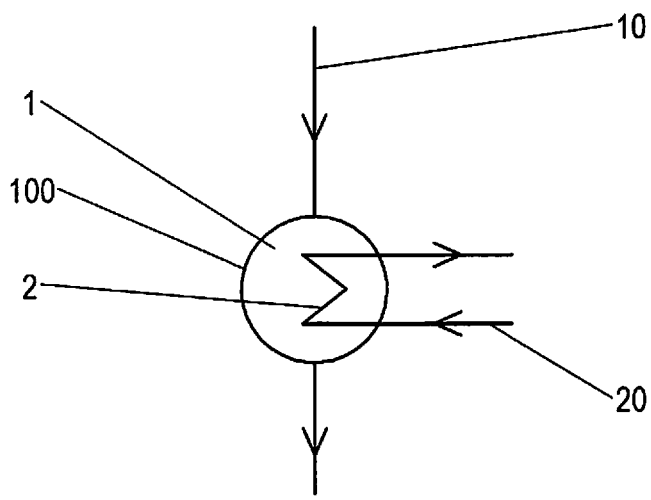
FIG. 1: a schematic view of the water inflow, of the dialyzate outflow and of the heat exchanger.

The fresh water inflow of a dialysis device is shown with the reference numeral 10 in FIG. 1. This fresh water is preferably RO water. The first space of the heat exchanger 100 is flowed through by this water and the schematically shown second space 2 is flowed through by consumed dialyzate which flows into the second space 2 through the line 20.

A heating of the RO water by consumed dialyzate takes place in this manner.

A heat-conductive and electrically insulating membrane is located between the two spaces 1 and 2 and is shown in the following Figures.

Figure 2:
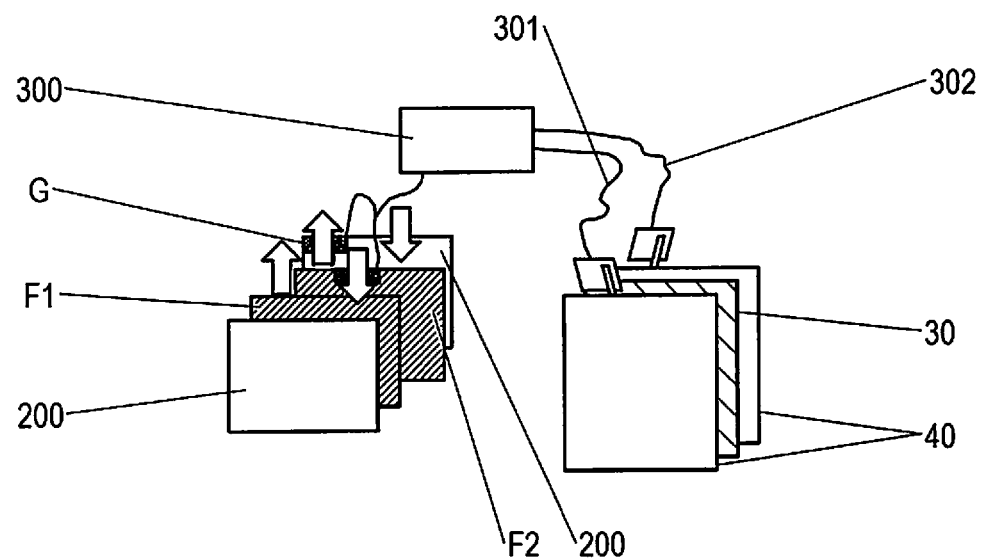
FIG. 2: a first variant of a direct electrical monitoring of the membrane.

FIG. 2 shows this membrane with the reference numeral 30. It is in this respect an electrical insulator which is adjacent to or is surrounded at both sides by metal layers 40 as capacitor plates. These two metallic layers can be formed, for example, by titanium membranes or steel membranes.

A possibility of monitoring the membrane 30 thus comprises the membrane being surrounded by two steel membranes or capacitor plates 40.

This overall arrangement of the membrane 30 and the plates 40 is arranged between the two fluid paths F1 and F2, wherein the fluid in accordance with fluid path F1 is the fresh water located in the first space 1 and the fluid in accordance with the fluid path F2 is the consumed dialyzate located in the second space 2.

Reference numeral 200 marks a housing of the arrangement of, for example, PPO (polyphenylene oxide) and reference symbol G marks the grounding of the two fluid paths F1 and F2.

An AC voltage source is marked by the reference numeral 300 which is electrically connected via the cables 301 and 302 to the capacitor plates 40 and applies an AC voltage to them.

Figure 3:
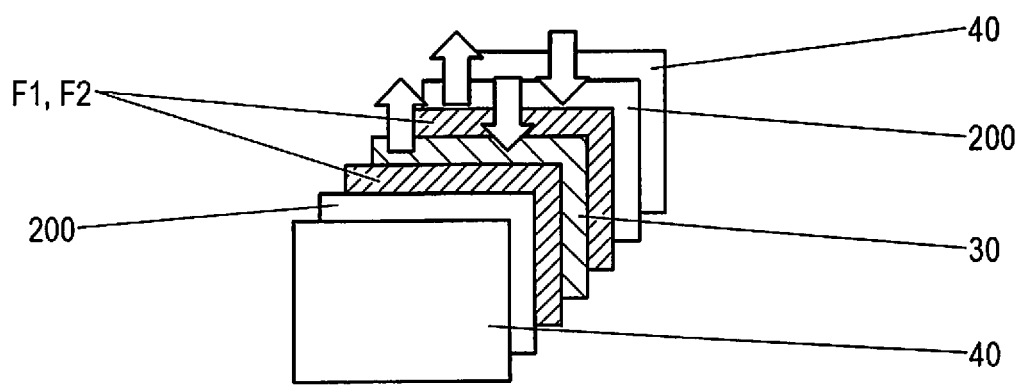
FIG. 3: a further realization possibility of the electrical membrane monitoring.

The realization possibility in accordance with FIG. 3 differs from that in accordance with FIG. 2 in that the capacitor plates 40 are not arranged between the two fluid paths F1 and F2, but rather enclose them. In other words, the fluid paths F1 and F2 are received between the two capacitor plates 40. The electrical insulator in the form of the membrane 30 is located between the fluid paths F1 and F2.

The housing is also marked by reference symbol 200 in accordance with FIG. 3.

In the variant in accordance with FIG. 3, an electrical insulator 30 having sufficient thermal conductivity is used as an internal membrane. A capacitor whose inner space which is designed with a dielectric is obtained by attaching electrically conductive plates 40 in the outer region.

In the case of an internal leak via the membrane 30, a liquid transfer takes place between the primary side and the secondary side, i.e. between the fluid paths F1 and F2. This liquid transfer has the consequence of a change of the dielectric properties. The resulting capacitance change can be measured and a leak which has occurred can thus be detected.

A capacitor is thus also configured overall in accordance with FIG. 3, wherein, unlike the embodiment in accordance with FIG. 2, fluid paths form a component of the capacitor.

All the variants shown are based on the principle of a varying impedance or capacitance in the case of a leak. All known possibilities for measuring these physical parameters or also other electrical or physical properties of the capacitor can thus be used to be able to draw a conclusion on a leak.

This also includes, for example, the integration of the capacitor into a resonant circuit and the shift of the resonant frequency associated with a leak.

Figure 4:
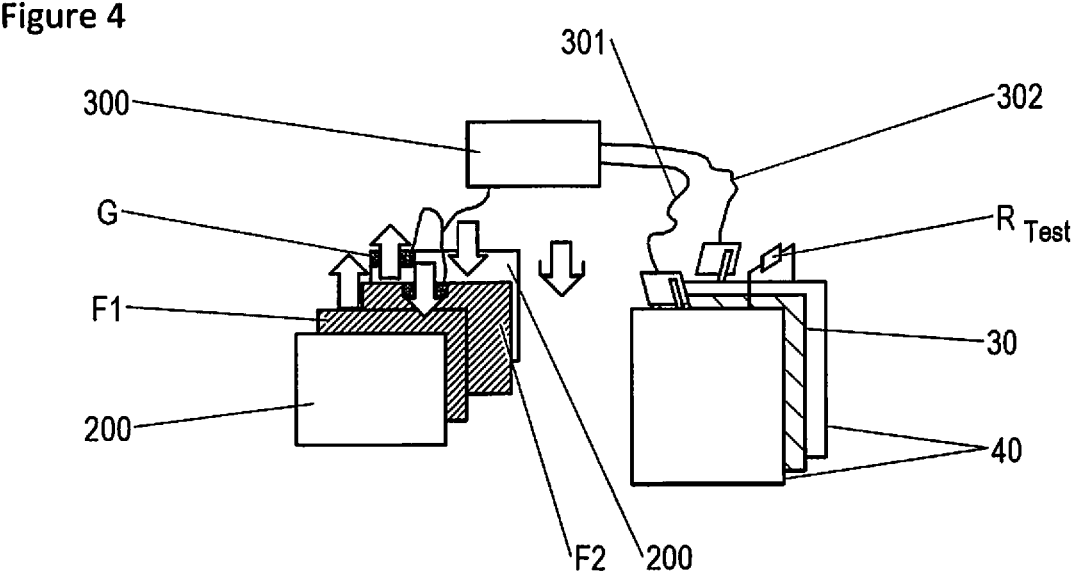
FIG. 4: a direct electrical monitoring of the membrane corresponding to FIG. 2 with a test resistor.

FIG. 4 shows an arrangement corresponding to FIG. 2 in which a test resistor is additionally connected between the two capacitor plates 40. This test resistor simulates a leak taking place over the membrane 30 and in this manner allows a correct check of the response of the monitoring means for such a leak.

The monitoring means can be formed, for example, by a measurement arrangement which is electrically connected to the capacitor plates 40 and which detects the AC or DC voltage and/or the current flow occurring between them.

Figure 5:
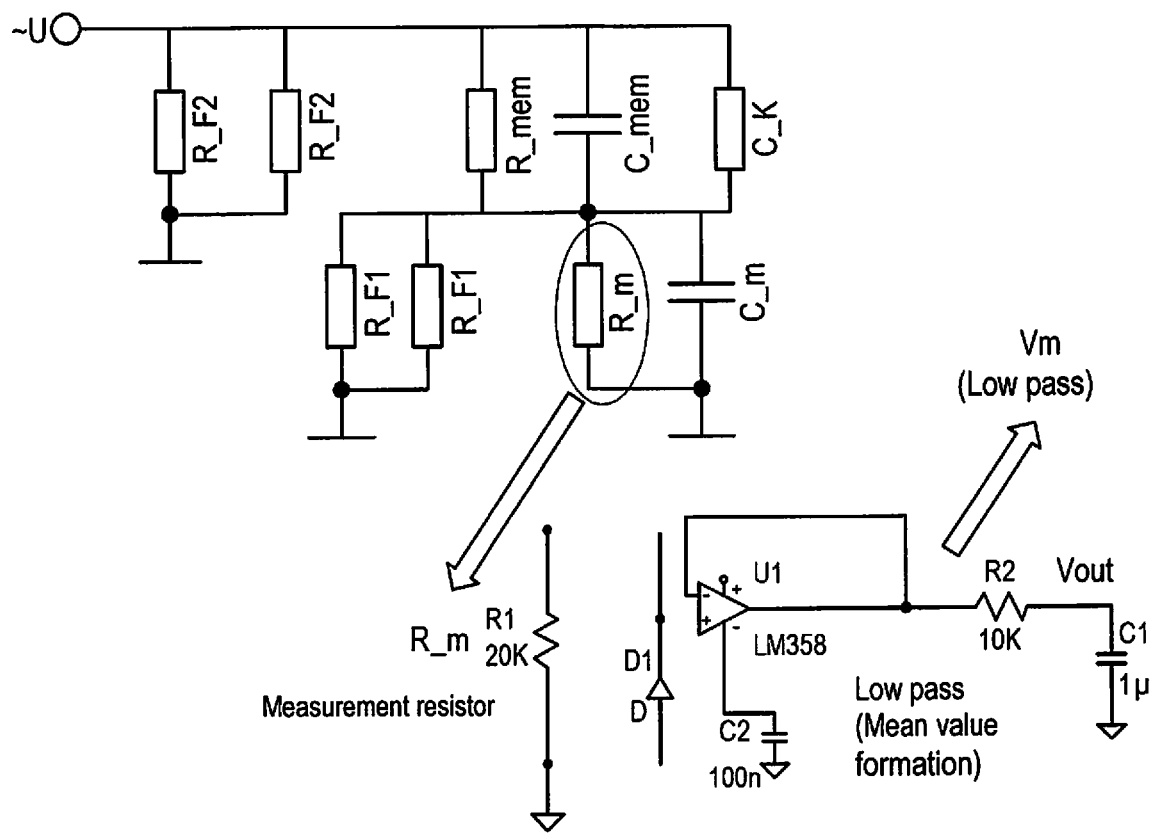
FIG. 5: a circuit diagram of the arrangement in accordance with FIG. 2 with a measurement resistor and a low pass filter for a voltage value determination.

FIG. 5 shows a circuit diagram of the arrangement in accordance with FIG. 2, wherein the parameter R_F2 is the ohmic resistance which is formed by the consumed dialyzate in accordance with F2 and the parameter F_F1 is the ohmic resistance which is formed by the fresh solution or the inflowing water in accordance with F1.

The parameter R_mem represents the ohmic resistance formed by the membrane and the parameter C_mem represents the capacitance of the capacitor formed by the capacitor plates 40 including the membrane 30.

The capacitance of the lines 301 and 302 is marked by C_K; the ohmic resistance of the measurement arrangement or of the monitoring means is marked by R_m; and their capacitance is marked by C_m.

As can be seen from FIG. 5, an AC voltage is applied at the input side.

A leak or the interposition of the test resistor results in a varied amplitude of the measured voltage and also in a higher voltage over the measurement resistor which can be determined by the mean value formation by the low pass in accordance with FIG. 5.

This average voltage value is marked by Vm in FIG. 5.

Figure 6:
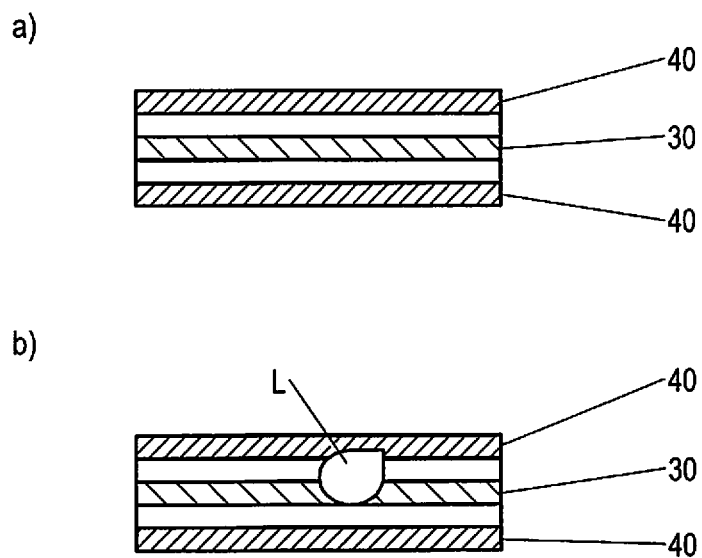
FIG. 6: a schematic view of a capacitor without and with a leak.

FIG. 6 shows in a schematic view in the image a) the membrane 30 which is surrounded like a sandwich by the two capacitor plates 40. No leak is present in the state a).

If a leak occurs which relates to the capacitor plate 40 and to the membrane 30, as can be seen from FIG. 6 b), an increased current flows through the measurement resistor R_m, whereby the measured voltage increases.

Figure 7:
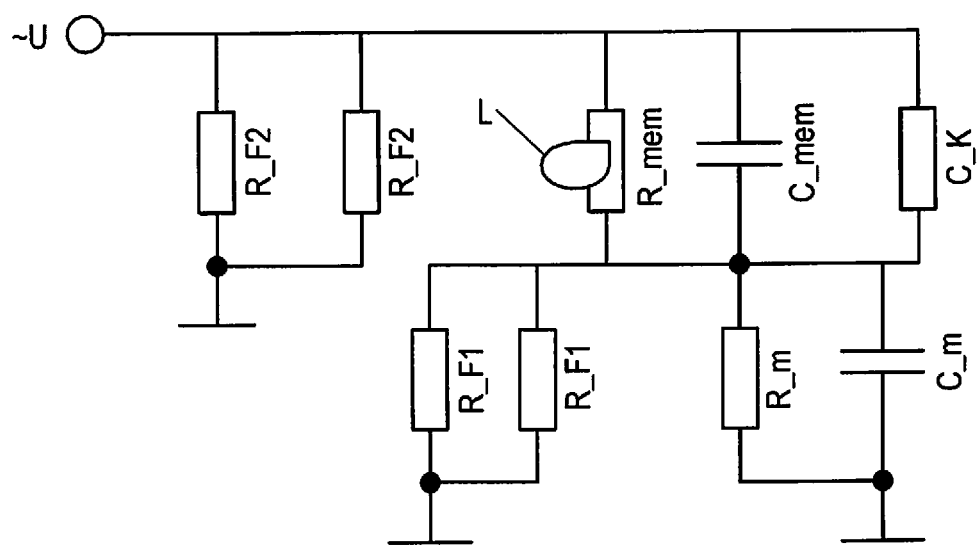
FIG. 7: a circuit diagram of the arrangement in accordance with FIG. 2 once a leak has occurred.

FIG. 7 shows the circuit in accordance with FIG. 5 once a leak L has occurred.

The occurrence of a leak case is thus directly measurable in this manner so that corresponding countermeasures can be taken. The monitoring means can, for example, initiate the closing of one or more valves and/or the stopping of one or more pumps.

A test of the arrangement in accordance with FIG. 5 can be carried out, for example, in that a higher sine amplitude produces a higher voltage value at the measurement resistor R_m.

The security of the monitoring in accordance with the invention is ensured in that a correspondingly lower signal is measured on a release of the cables 301 or 302 or on an absence of the voltage supply.

The monitoring of at least one physical or electrical parameter, which is preferably carried out continuously by the monitoring means, makes it possible to detect the variation of the measured variable, such as the impedance or the capacitance of the capacitor, directly in the event of a leak at the membrane or at the capacitor plates.

A preferred embodiment of the invention comprises the fact that the capacitor which comprises at least two plates and at least one insulator in the form of a membrane arranged therebetween is located between the two spaces of the heat exchanger or recuperator. In this case, the capacitor separates the two fluid paths or the first space and the second space of the heat exchanger.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A blood treatment device comprising:
   a heat exchanger having
   a first space and a second space, through which, during operation of the blood treatment device, a first fluid flows through the first space and a second fluid flows through the second space,
   a membrane which separates the first space from the second space, the membrane forming a component of a capacitor which has a first capacitor plate and a second capacitor plate, between which the membrane is located,
   a monitor which is connected to the capacitor and which is configured to detect an electrical property of the capacitor so as to detect a leak of the first fluid from the first space to the second space, and
   a test resistor for checking the monitor, the test resistor being connected in parallel with the resistor formed by the membrane.

2. The blood treatment device in accordance with claim 1, wherein the first capacitor plate and the second capacitor pate and the membrane are located between the first space and the second space.

3. The blood treatment device in accordance with claim 1, wherein the membrane is located between the first space and the second space, and the first space and the second space are arranged between the first capacitor plate and the second capacitor plate.

4. The blood treatment device in accordance with claim 1, wherein the monitor includes a DC or a AC voltage source having poles connected to the first capacitor plate and the second capacitor plate.

5. The blood treatment device in accordance with claim 1, wherein the first capacitor plate and the second capacitor plat contact the membrane directly and at both sides thereof to provide a sandwich-like structure.

6. The blood treatment device in accordance with claim 1, wherein the first capacitor plate and the second capacitor plate include a metal and/or the membrane is configured as an electrical insulator.

7. The blood treatment device in accordance with claim 1, wherein the monitor is configured to effect an impedance measurement or a capacitance measurement of the capacitor.

8. The blood treatment device in accordance with claim 1, wherein the capacitor is integrated into a resonant circuit and the monitor is configured to effect a measurement of a resonant frequency of the capacitor.

9. The blood treatment device in accordance with claim 1, wherein the monitor includes a measurement resistor over which a voltage is determined.

10. The blood treatment device in accordance with claim 9, wherein the measurement resistor is connected in series with the resistor provided by the membrane.

11. The blood treatment device in accordance with claim 9, wherein the monitor has a low pass filter for determining an average value of the voltage.

12. The blood treatment device in accordance with claim 9, wherein the blood treatment device is a dialysis device.

13. The blood treatment device in accordance with claim 12, wherein the blood treatment device is connected to a water supply, and the heat exchanger is connected to the water supply such that fresh water flows through the first space of the heat exchanger.

14. The blood treatment device in accordance with claim 12, wherein the second space of the heat exchanger is arranged such that consumed dialysis solution flows therethrough.

15. The blood treatment device according to claim 6, wherein the metal is steel or titanium.

16. The blood treatment device according to claim 6, wherein the electrical insulator includes Kapton.

17. The blood treatment device according to claim 13, wherein the fresh water is RO water from the water supply.

* * * * *